United States Patent
Wismer

(10) Patent No.: US 9,284,241 B2
(45) Date of Patent: Mar. 15, 2016

(54) PROCESS FOR THE REMOVAL OF CONTAMINANT FROM A HYDROCHLOROFLUOROOLEFIN BY EXTRACTIVE DISTILLATION

(71) Applicant: Arkema Inc., King of Prussia, PA (US)

(72) Inventor: John A. Wismer, Washington Crossing, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 14/381,011

(22) PCT Filed: Feb. 22, 2013

(86) PCT No.: PCT/US2013/027205
§ 371 (c)(1),
(2) Date: Aug. 26, 2014

(87) PCT Pub. No.: WO2013/130342
PCT Pub. Date: Sep. 6, 2013

(65) Prior Publication Data
US 2015/0005539 A1    Jan. 1, 2015

Related U.S. Application Data

(60) Provisional application No. 61/605,883, filed on Mar. 2, 2012.

(51) Int. Cl.
*C07C 17/386* (2006.01)
*B01D 3/40* (2006.01)

(52) U.S. Cl.
CPC ............. *C07C 17/386* (2013.01); *B01D 3/40* (2013.01); *C07B 2200/07* (2013.01)

(58) Field of Classification Search
CPC ...... C07C 17/386; B01D 3/40; C07B 2200/07
USPC .................................................. 570/177, 178
See application file for complete search history.

(56) References Cited

U.S. PATENT DOCUMENTS

| | | | |
|---|---|---|---|
| 6,264,399 B1 | 7/2001 | Grisso et al. | |
| 2010/0237279 A1 | 9/2010 | Hulse et al. | |
| 2011/0101264 A1* | 5/2011 | Knapp | 252/67 |
| 2011/0270001 A1 | 11/2011 | Ishihara et al. | |
| 2013/0105296 A1* | 5/2013 | Chaki et al. | 203/60 |

FOREIGN PATENT DOCUMENTS

WO    WO 95/21147    8/1995

* cited by examiner

*Primary Examiner* — Shailendra Kumar
(74) *Attorney, Agent, or Firm* — Steven D. Boyd

(57) ABSTRACT

A method for removing a contaminant from a hydrochlorofluoroolefin (such as trans-1,1,1-trifluoro-3-chloro-2-propene (1233zd(E))) includes extracting a chlorofluorocarbon (such as trichlorofluoromethane (R11)) from a mixture comprising the hydrochlorofluoroolefin and the chlorofluorocarbon using extractive distillation in the presence of an extractive solvent comprising a chlorinated compound to form a purified hydrochlorofluoroolefin. This separation method provides for removal of a contaminant, such as R11, from a hydrochlorofluoroolefin, such as 1232zd(E), which are not separable by conventional distillation methods. The method may employ a process utilizing two distillation columns, for example, a first extractive distillation column and a second solvent recovery column, which allows for recycle of the extractive solvent to the first extractive distillation column.

20 Claims, 1 Drawing Sheet

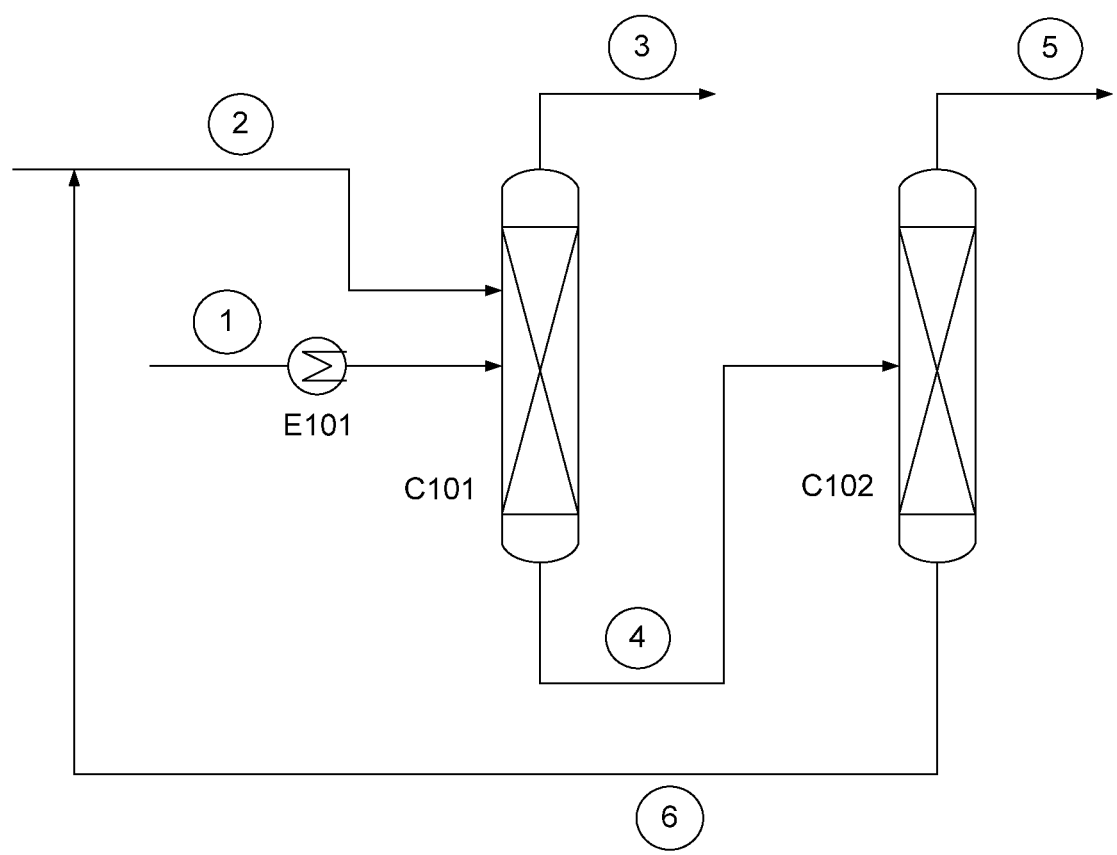

PROCESS FOR THE REMOVAL OF CONTAMINANT FROM A HYDROCHLOROFLUOROOLEFIN BY EXTRACTIVE DISTILLATION

The present application claims priority to International Application serial number PCT/US2013/027205 filed Feb. 22, 2013, which claims priority to U.S. provisional application Ser. No. 61/605,883 filed Mar. 2, 2012.

FIELD OF THE INVENTION

The invention relates to a method of extracting and removing contaminants, such as trichlorofluoromethane (R1"), from a mixture containing a hydrochlorofluoroolefin, such as trans-1,1,1-trifluoro-3-chloro-2-propene (1233zd(E)).

BACKGROUND OF THE INVENTION

Chlorine-containing compounds such as chlorofluorocarbons (CFCs) are considered to be detrimental to the Earth's ozone layer. Therefore, compounds that do not damage the environment, but also possess the properties necessary to function as refrigerants, solvents, cleaning agents, foam blowing agents, aerosol propellants, heat transfer media, dielectrics, fire extinguishing agents, sterilants and power cycle working fluids, have been investigated. Fluorinated olefins, especially those containing one or more hydrogens in the molecule (referred to herein as hydrofluoroolefins (HFOs)) are being considered for use in some of these applications, such as in refrigeration as well as in processes to make fluoropolymers. In particular, trans-1,1,1-trifluoro-3-chloro-2-propene (1233zd(E)) is a potential refrigerant and foam blowing compound that has negligible ozone depletion potential (ODP) and low global warming potential (GWP). In fact, 1233zd(E)'s ODP has been measured as 0.00034.

1233zd(E) feedstock is usually contaminated with carbon tetrachloride, however, which is one of the precursor compounds to 1,1,1,3,3-pentachloropropane (240fa). In a fluorination reactor, the carbon tetrachloride will fluorinate to R11. R11 has a boiling point of 23.8° C. and 1233zd(E) has a boiling point of 18.5° C. Attempts to separate R11 from 1233zd(E) by distillation were unsuccessful, indicating the presence of an azeotrope or near azeotrope. A contaminant, such as R11, which has an ODP of 1.0, can greatly decrease the ozone depletion potential of the compound. For example, if 1233zd(E) is contaminated with merely 1000 ppm of R11, its ODP would increase from 0.00034 to 0.00134. Accordingly, there remains a need for 1233zd(E) in uncontaminated or purified form and a separation method by which to produce it.

SUMMARY OF THE INVENTION

The methods according to the present invention provide extractive distillation methods suitable for separating a contaminant from a hydrochlorofluoroolefin. In particular, the methods and process described herein provide for an effective way to separate a contaminant from a mixture that cannot be separated by conventional distillation. For example, 1233zd (E) and R11 are not separable by conventional distillation, but the extractive distillation methods described herein using a chlorinated compound can be used to extract the R11 away from the 1233zd(E).

According to an embodiment of the present invention, a method for removing a contaminant from a hydrochlorofluoroolefin includes extracting a chlorofluorocarbon from a mixture comprising a hydrochlorofluoroolefin and the chlorofluorocarbon using extractive distillation in the presence of an extractive solvent comprising a chlorinated compound to form a purified hydrochlorofluoroolefin.

According to another embodiment of the present invention, a method for removing a contaminant from a hydrochlorofluoroolefin includes extracting trichlorofluoromethane (R11) from a mixture comprising the trichlorofluoromethane (R11) and trans-1,1,1-trifluoro-3-chloro-2-propene (1233zd(E)) using extractive distillation in the presence of an extractive solvent comprising a chlorinated compound to form a purified trans-1,1,1-trifluoro-3-chloro-2-propene (1233zd(E)).

According to another embodiment of the present invention, a distillation process includes feeding a feed mixture comprising a hydrochlorofluoroolefin comprising a contaminant to a first extractive distillation column and extracting the contaminant from the feed mixture in the first extractive distillation column using an extractive solvent comprising a chlorinated compound to form an overhead stream comprising a purified hydrochlorofluoroolefin and a bottoms stream comprising the contaminant and the extractive solvent. A second step may be employed whereby the bottoms stream is fed to a second distillation column and the contaminant is separated from the extractive solvent in the second distillation column to form a second overhead stream comprising the contaminant and a second bottoms stream comprising the extractive solvent. If desired, the second bottoms stream comprising the extractive solvent may then be recycled to the first distillation column to be used in the first distillation column, i.e., the extractive distillation process.

According to another embodiment of the present invention, a distillation process includes feeding a feed mixture comprising trichlorofluoromethane (R11) and trans-1,1,1-trifluoro-3-chloro-2-propene (1233zd(E)) to a first extractive distillation column and extracting the trichlorofluoromethane (R11) from the feed mixture in the first extractive distillation column using an extractive solvent comprising a chlorinated compound to form an overhead stream comprising a purified trans-1,1,1-trifluoro-3-chloro-2-propene (1233zd(E)) and a bottoms stream comprising the trichlorofluoromethane (R11) and the extractive solvent. Optionally, the bottoms stream may be fed to a second distillation column, and the trichlorofluoromethane (R11) may be separated from the extractive solvent in the second distillation column to form a second overhead stream comprising the trichlorofluoromethane (R11) and a second bottoms stream comprising the extractive solvent. The extractive solvent may be recycled as needed in the first extractive distillation column.

BRIEF DESCRIPTION OF THE DRAWING

The invention may be further understood by reference to a drawing in which FIG. 1 depicts a flowchart of an extractive distillation process in accordance with the invention.

DETAILED DESCRIPTION OF THE INVENTION

Aspects of the present invention include methods and processes for distilling hydrochlorofluoroolefins, such as trans-1,1,1-trifluoro-3-chloro-2-propene (1233zd(E)), and removing contaminants, such as trichlorofluoromethane (R11), therefrom.

According to one embodiment of the present invention, a method for removing a contaminant from a hydrochlorofluoroolefin includes extracting a chlorofluorocarbon (such as trichlorofluoromethane (R11)) from a mixture comprising a hydrochlorofluoroolefin (such as trans-1,1,1-trifluoro-3- chloro-2-propene (1233zd(E))) and the chlorofluorocarbon (e.g., R11) using extractive distillation in the presence of an extractive solvent comprising a chlorinated compound to form a purified hydrochlorofluoroolefin (e.g., purified 122zd (E)).

As used herein, HCC designates hydrochlorocarbons, CFC designates chlorofluorocarbons, and HCFO designates hydrochlorofluoroolefins. Each species may be discussed interchangeably with respect to its chemical formula, chemical name, abbreviated common name, etc. For example, trans-1,1,1-trifluoro-3-chloro-2-propene may be designated as 1233zd(E). Also, some compounds may be described with respect to their ASHRAE (American Society of Heating, Refrigerating and Air-Conditioning Engineers) designations. Table 1 provides a representative list.

TABLE 1

| 1,1,1,3,3-pentachloropropane | $C_3H_3Cl_5$ | HCC-240fa | 240fa |
|---|---|---|---|
| trichlorofluoromethane | $CCl_3F$ | CFC-11 | R11 |
| trans-1,1,1-trifluoro-3-chloro-2-propene (also known as trans 1-chloro-3,3,3-trifluoropropene) | $C_3H_2ClF_3$ | HCFO-1233zd(E) | 1233zd(E) or E-1233zd |

Each compound described herein, unless designated otherwise, includes its different isomers and stereoisomers, including all single configurational isomers, single stereoisomers, and any combination thereof in any ratio.

The present invention includes a method for removing a contaminant from a hydrochlorofluoroolefin. Hydrochlorofluoroolefins, such as 1233zd(E), are often contaminated by reactants or intermediates formed during their production. For example, the manufacture of 1233zd(E) typically uses 1,1,1,3,3 pentachloropropane (240fa) as a feedstock. 240fa is usually contaminated with carbon tetrachloride, which is one of the precursor compounds to 240fa. In a fluorination reactor, the carbon tetrachloride will fluorinate to R11. As discussed above, a contaminant, such as R11, which has an ODP of 1.0, can greatly decrease the ozone depletion potential of the compound. For example, if 1233zd(E) were contaminated with merely 1000 ppm of R11, its ODP would increase from 0.00034 to 0.00134. Accordingly, it is desirous to separate and remove the contaminant from the hydrochlorofluoroolefin, for example, to produce 1233zd(E) in uncontaminated or purified form and improve and decrease its ozone depletion potential. Accordingly, the contaminant may include any compounds or precursor compounds remaining in the hydrochlorofluoroolefin. In a particular embodiment where 1233zd (E) is the hydrochlorofluoroolefin, the contaminant may comprise at least one of carbon tetrachloride and trichlorofluoromethane (R11).

The method may include extracting a chlorofluorocarbon (a contaminant such as trichlorofluoromethane (R11)) from a mixture comprising a hydrochlorofluoroolefin (such as trans-1,1,1-trifluoro-3-chloro-2-propene (1233zd(E))) and the chlorofluorocarbon (e.g., R11). The mixture may be obtained from any suitable source. For example, the hydrochlorofluoroolefin may be obtained directly after synthesis and the hydrochlorofluoroolefin may be synthesized by any suitable methods and techniques known to one of ordinary skill in the art.

For example, 1233zd(E) may be obtained from a fluorination reaction. In one embodiment, 1,1,1,3,3-pentachloropropane (240fa) and/or 1,1,3,3-tetrachlororopropene (1230za) is fluorinated to form trans 1233zd (1233zd(E)) and/or cis 1233zd (1233zd(Z)). For example, the reaction where 240fa is fluorinated to 1233zd(E) may be depicted as follows:

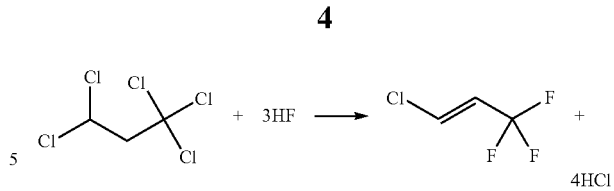

If necessary, the 1233zd(E) may be separated from the 1233zd(Z) using any techniques known to one of ordinary skill in the art. The fluorination reaction may be gas or liquid phase and may be catalyzed or uncatalyzed. Suitable fluorination catalysts may be selected by one of ordinary skill in the art, such as $TiCl_4$, $TiF_4$, $SnCl_4$, $SnF_4$, $SbF_5$, $SbCl_5$, $SbF_xCl_y$ (x+y=5), or the like.

The reactions described herein may be conducted in any suitable reaction vessel or reactor. The vessel or reactor may be of any suitable type, shape, and size. For example, the reactor may be a fixed or fluid catalyst bed reactor, a tubular reactor, etc. The reactions may be carried out batch wise, continuous, or any combination of these. The reactions may be performed using a wide variety of process parameters and process conditions readily ascertainable to one of ordinary skill in the art based on the teachings provided herein.

The operating conditions and residence times of the reactants in the reactor should be sufficient for the reactions to take place with an acceptable yield (including conversion efficiency and selectivity), which may be determined as a function of the operating conditions adopted. The reaction pressure can be subatmospheric, atmospheric, or superatmospheric. If a catalyst is used during the reaction and the catalyst deactivates over time, it may be replaced or regenerated using any suitable techniques known in the art.

The contaminant (e.g., carbon tetrachloride and/or trichlorofluoromethane (R11)) may be extracted using extractive distillation in the presence of an extractive solvent comprising a chlorinated compound to form a purified hydrochlorofluoroolefin (e.g., purified 1233zd(E)). The pure, purified, or uncontaminated hydrochlorofluoroolefin contains less contaminant than the feed comprising the hydrochlorofluoroolefin. For example, purified 1233zd(E) may comprise up to 30% less, up to 50% less, up to 75% less, or up to 100% less than the amount of contaminant present in the feed stock. Preferably, none or only negligible amounts of the contaminant(s) remain and a pure hydrochlorofluoroolefin product results (e.g., the purified 1233zd(E) comprises about 500 ppm or less, preferably 300 ppm or less, more preferably 200 ppm or less, most preferably 100 ppm or less of the chlorofluorocarbon).

As used herein "extractive distillation" includes a process operation (e.g., vapor-liquid or liquid-liquid) that uses a third component, or separation solvent, to effect a chemical separation. The extractive agent creates or enhances the volatility difference between the components to be separated and does not form an azeotrope with the other components in the mixture. This enables a new three-part mixture to be separated by normal distillation. The original component with the greatest volatility separates out as the top product or distillate (e.g., 1233zd(E)). The bottom product consists of a mixture of the extractive solvent and the other component (e.g., extractive solvent plus R11), which can again be separated easily because the solvent does not form an azeotrope with the contaminant (e.g., R11). The bottom product can be separated by any suitable methods known in the art (e.g., separation may be accomplished by distillation, membrane separation, adsorption, and the like).

As used herein "extractive agent," "separation solvent," or "extractive solvent" may be used interchangeably to define a solvent that is relatively nonvolatile, has a high boiling point, and is miscible with the contaminated hydrochlorofluoroolefin, but does not form an azeotropic mixture. The extractive solvent comprises a chlorinated compound. For example, the extractive solvent may comprise an organochloride, chlorinated hydrocarbon, or chloroalkane. In particular, the extractive solvent may comprise an organic compound containing at least one covalently bonded chlorine atom. Preferably, the extractive solvent comprises an organochloride comprising at least three chlorine atoms (e.g., three or four chlorine atoms). The extractive solvent may, for example, comprise one or two carbon atoms. Where the extractive solvent contains two or more carbon atoms, the solvent may be saturated or unsaturated. In one embodiment, the extractive solvent does not contain any elements other than carbon, chlorine, and, optionally, hydrogen. In an exemplary embodiment, the extractive solvent comprises an organochloride selected from the group consisting of trichloroethylene ($C_2HCl_3$) (TCE), carbon tetrachloride or tetrachloromethane ($CCl_4$), chloroform ($CHCl_3$), methyl chloroform or 1,1,1-trichloroethane ($CH_3CCl_3$), and mixtures thereof.

The extractive solvent may be selected based on the solvent's boiling point relative to the contaminant's boiling point. For example, R11 has a boiling point of 23.8° C. In one embodiment, the solvent may be selected to have a boiling point significantly greater than that of R11 but not so great that it cannot be distilled under a positive pressure. Accordingly, suitable extractive solvents may have a normal boiling point of about 60° C. or greater. For example, the normal boiling point may be between about 60° C. and about 100° C. or between about 60° C. and about 90° C. The normal boiling points of suitable solvents include trichloroethylene (nbp=88° C.), carbon tetrachloride (nbp=76.8° C.), chloroform (nbp=61.2° C.), and methyl chloroform (74.1° C.), for example.

The amount of extractive solvent should be suitable to provide for an effective and efficient extractive distillation. The amount of extractive solvent may be selected by one of ordinary skill in the art based on the amount of hydrochlorofluoroolefin present in the feed stock. For example, the amount of extractive solvent may be based on a weight ratio of the extractive solvent to the feed stock of hydrochlorofluoroolefin. In one embodiment of the invention, a weight ratio of the extractive solvent/1233zd(E) is about 0.1 to 10, preferably about 1 to 8, more preferably about 1 to 5, most preferably about 1 to 3.

The extractive distillation may be performed under any suitable conditions (e.g., temperatures and pressures) using suitable equipment (e.g., a distillation column) known to one of ordinary skill in the art. For example, the extractive distillation may be performed under standard temperature and pressure. Alternatively, the extractive distillation may be performed under a vacuum or positive pressure using temperatures ranging from about 26° C. to about 120° C. The extractive distillation may be performed batch wise, continuous, or any combination of these. The distillation column may contain trays and/or may be packed (e.g., with an inert packing material such as glass beads or metal pieces, such as Raschig rings) or unpacked. The packing may be random or structured. For example, structured packing may include corrugated metal sheets or knitted metal filaments. The packing may be positioned along the entire column, below the feed point, or over some other area along the length of the column, for example.

According to one embodiment of the present invention, a method for removing a contaminant from a hydrochlorofluoroolefin includes extracting trichlorofluoromethane (R11) from a mixture comprising the trichlorofluoromethane (R11) and trans-1,1,1-trifluoro-3-chloro-2-propene (1233zd(E)) using extractive distillation in the presence of an extractive solvent comprising a chlorinated compound to form a purified trans-1,1,1-trifluoro-3-chloro-2-propene (1233zd(E)).

According to another embodiment of the present invention, a distillation process includes feeding a feed mixture comprising a hydrochlorofluoroolefin comprising a contaminant to a first distillation column; and extracting the contaminant from the feed mixture in the first distillation column using an extractive solvent comprising a chlorinated compound to form an overhead stream comprising a purified hydrochlorofluoroolefin and a bottoms stream comprising the contaminant and the extractive solvent.

An embodiment depicted in FIG. 1 shows a first column C101, which combines a feed (stream 1) with sufficient solvent (stream 6 and optional recycle stream 2) to provide a host for the R11. The feed stream 1 may comprise a mixture comprising the hydrochlorofluoroolefin and the contaminant (e.g., 1233zd(E) and R11). As noted above, a suitable weight ratio of extractive solvent to 1233zd(E) feed can be selected (e.g., about 0.1 to 10) to be fed to the distillation column. Pure 1233zd(E) (steam 3) is the overhead of the first column C101 while the extractive solvent containing R11 is the bottoms (stream 4).

The feed stock and extractive solvent may be introduced at any suitable point on the distillation column in any suitable form (e.g., liquid or gas phase). For example, both the feedstock and the extractive solvent may be introduced at the center of the distillation column or at some other point along the length of the column Subsequent to the extractive distillation process, one or more (e.g., a series) distillation or separation processes may be employed. For example, the bottoms stream from the first distillation column may be fed to a second distillation column, and the contaminant may be separated from the extractive solvent in the second distillation column to form a second overhead stream comprising the contaminant and a second bottoms stream comprising the extractive solvent. The second overhead stream may also include substantial amounts of the feed to the second distillation column (e.g., remaining hydrochlorofluoroolefin and solvent). For example, the second overhead stream may contain more feed than contaminant while still functioning effectively for extracting the contaminant during the distillation.

Thus, in one embodiment, the extractive distillation includes two distillation columns in series (a first extractive distillation and a second normal distillation). The 1233zd(E) is fed in stream 1. The solvent can either be included in stream 1 or fed as its own stream 2, normally at a feed point above stream 1. The embodiment depicted in FIG. 1 shows the bottoms stream (stream 4) from the first extractive distillation column C101 becomes the feed to the second solvent recovery column C102. The second column C102 strips off R11 as an overhead (stream 5, which also contains feed to the second solvent recovery column C102) and recovers the regenerated extractive solvent (stream 6). Optionally, the extractive solvent from the second bottoms stream 6 is recycled to the first distillation column C101 to be used in the extractive distillation process therein.

It is also envisioned that additional distillations or separations may be employed as necessary to arrive at the desired purity for each of the product/waste streams. For example, each of the overhead stream(s) may be further distilled/separated to remove any residual contaminant, hydrochlorofluoroolefin, or extractive solvent and/or the bottoms stream may be further distilled/separated to improve the purity of the extractive solvent, if necessary.

According to one embodiment of the invention, a distillation process includes:

(a) feeding a feed mixture comprising trichlorofluoromethane (R11) and trans-1,1,1-trifluoro-3-chloro-2-propene (1233zd(E)) to a first distillation column;

(b) extracting the trichlorofluoromethane (R11) from the feed mixture in the first distillation column using an extractive solvent comprising a chlorinated compound to form an overhead stream comprising a purified trans-1,1,1-trifluoro-3-chloro-2-propene (1233zd(E)) and a bottoms stream comprising the trichlorofluoromethane (R11) and the extractive solvent;

(c) feeding the bottoms stream to a second distillation column; and (d) separating the trichlorofluoromethane (R11) from the extractive solvent in the second distillation column to form a second overhead stream comprising the trichlorofluoromethane (R11) and a second bottoms stream comprising the extractive solvent.

The methods and processes described herein provide for extractive distillation suitable for separating a contaminant, such as R11, from a hydrochlorofluoroolefin, such as 1233zd (E), which could not be readily separated by conventional distillation techniques. Thus, a purified hydrochlorofluoroolefin, such as 1233zd(E), may be obtained and used having a reduced ozone depletion potential and low global warming potential for applications such as a refrigerant, foam blowing compound, or the like.

EXAMPLES

Comparative Example 1

A sample of 1233zd(E) was fed to the center of a distillation column. Below the feed point was 8 ft of 3 inch diameter Goodloe packing. An identical section of packing extended for 8 ft above the feed point. The column was capped by a 7 square ft partial reflux condenser. The feed rate to the column was 32 pounds per hour and the reflux rate was 120 pounds per hour. The distillate (overhead) rate was 30 pounds per hour and the bottoms rate was 2 pounds per hour. The distillation pressure was 55 psig. The following analysis was obtained for the respective streams:

TABLE 1

|  | Feed | Ovhd | Btms |
|---|---|---|---|
|  |  | wt % |  |
| 1233zd(E) | 99.8720 | 99.7758 | 99.8765 |
| R11 | 0.0785 | 0.0721 | 0.0831 |
| Other | 0.0495 | 0.1521 | 0.0404 |

The example in Table 1 shows an 8.9% reduction in R11 content at a 93.75% 1233zd(E) recovery.

Example 2

The equipment described above in Comparative Example 1 was used to undertake an extractive distillation using trichloroethylene (TCE) as an extractive solvent. The 1233zd(E) feed stream (Stream 1) was fed at a rate of 20 pounds per hour, the TCE feed stream (Stream 2) was fed at a rate of 30 pounds per hour, the overhead distillate stream (Stream 3) rate was 18 pounds per hour and the bottoms stream (Steam 4) flow rate was 32 pounds per hour. The reflux rate was 100 pounds per hour and the column pressure was 36 psig. At the time samples were taken for analysis, the reboiler temperature was 114.6° C. and the top of the column below the condenser was 53° C. The volumetric capacity of the reboiler was about 40 pounds of liquid TCE, which made a steady state difficult to achieve in a reasonable run time. The extraction solvent to 1233zd(E) weight ratio was 1.5 to 1. The 1233zd feed point was at the center of the column through a steam heated heat exchanger. The TCE solvent was fed at ambient temperature to a point half way between the column top and column center. The reflux ratio of the column was 5.55 based on distillate. Samples were taken 2.5 hours after the initial charge to the column. There was a 49% reduction in R11 content at a 90% 1233zd(E) recovery. Table 2 summarizes the results. The material balance shows that only 95% of the 1233zd(E) and 80% of the R11 fed into the system was accounted for in the effluent. This means that the system had not yet achieved steady state conditions. Nonetheless the data shows the enhancement of R11 relative to 1233zd in the bottoms (from 0.22% in feed to 1.38% based on F1233zd) and the removal of R11 from the overhead via extractive distillation.

TABLE 2

|  | 1233zd Feed | TCE Feed | Overhead 1233ZD | Bottoms |
|---|---|---|---|---|
|  |  |  | wt % |  |
| TCE | 0.0000 | 99.4 | 0.0000 | 95.6836 |
| F1233zd | 99.6660 |  | 99.7876 | 3.4132 |
| R11 | 0.2215 |  | 0.1131 | 0.0472 |
| Other | 0.1125 | 0.6 | 0.0993 | 0.8560 |

What is claimed:

1. A method for removing a contaminant from a hydrochlorofluoroolefin comprising:
   extracting a chlorofluorocarbon from a mixture comprising a hydrochlorofluoroolefin and the chlorofluorocarbon using extractive distillation in the presence of an extractive solvent comprising an organochloride selected from the group consisting of carbon tetrachloride, chloroform, methyl chloroform, and mixtures thereof to form a purified hydrochlorofluoroolefin.

2. A method according to claim 1, wherein the organochloride is comprised of at least three chlorine atoms.

3. A method according to claim 1, wherein the extractive solvent has a normal boiling point between about 60° C. and about 100° C.

4. A method according to claim 1, wherein the hydrochlorofluoroolefin comprises trans-1,1,1-trifluoro-3-chloro-2-propene (1233zd(E)).

5. A method according to claim 4, wherein the purified hydrochlorofluoroolefin is purified trans-1,1,1-trifluoro-3-chloro-2-propene (1233zd(E)) comprising about 500 ppm or less of the chlorofluorocarbon.

6. A method according to claim 1, wherein the contaminant comprises at least one of carbon tetrachloride and trichlorofluoromethane (R11).

7. A method for removing a contaminant from a hydrochlorofluoroolefin comprising:
   extracting trichlorofluoromethane (R11) from a mixture comprising the trichlorofluoromethane (R11) and trans-1,1,1-trifluoro-3-chloro-2-propene (1233zd(E)) using extractive distillation in the presence of an extractive solvent comprising an organochloride selected from the group consisting of carbon tetrachloride, chloroform, methyl chloroform, and mixtures thereof to form a purified trans-1,1,1-trifluoro-3-chloro-2-propene (1233zd(E)).

8. A method according to claim 7, wherein the organochloride is comprised of three or four chlorine atoms.

9. A method according to claim 7, wherein the organochloride is comprised of 1 or 2 carbon atoms.

10. A method according to claim 7, wherein the extractive solvent has a normal boiling point of about 60° C. or greater.

11. A method according to claim 7, wherein a weight ratio of the extractive solvent to 1233zd(E) is about 0.1 to 10.

12. A method according to claim 11, wherein the extractive solvent to 1233zd(E) weight ratio is about 1 to 3.

13. A purified trans-1,1,1-trifluoro-3-chloro-2-propene (1233zd(E)) obtained in accordance with the method of claim 7.

14. A distillation process comprising:
feeding a feed mixture comprising a hydrochlorofluoroolefin comprising a contaminant to a first distillation column; and
extracting the contaminant from the feed mixture in the first distillation column using an extractive solvent comprising an organochloride selected from the group consisting of carbon tetrachloride, chloroform, methyl chloroform, and mixtures thereof to form an overhead stream comprising a purified hydrochlorofluoroolefin and a bottoms stream comprising the contaminant and the extractive solvent.

15. A process according to claim 14 further comprising:
feeding the bottoms stream to a second distillation column; and
separating the contaminant from the extractive solvent in the second distillation column to form a second overhead stream comprising the contaminant and a second bottoms stream comprising the extractive solvent.

16. A process according to claim 14, wherein the contaminant comprises at least one of carbon tetrachloride and trichlorofluoromethane (R11).

17. A process according to claim 14, wherein the hydrochlorofluoroolefin comprises trans-1,1,1-trifluoro-3-chloro-2-propene (1233zd(E)).

18. A process according to claim 15, wherein the extractive solvent from the second bottoms stream is recycled to the first distillation column.

19. A distillation process comprising:
feeding a feed mixture comprising trichlorofluoromethane (R11) and trans-1,1,1-trifluoro-3-chloro-2-propene (1233zd(E)) to a first distillation column;
extracting the trichlorofluoromethane (R11) from the feed mixture in the first distillation column using an extractive solvent comprising an organochloride selected from the group consisting of carbon tetrachloride, chloroform, methyl chloroform, and mixtures thereof to form an overhead stream comprising a purified trans-1,1,1-trifluoro-3-chloro-2-propene (1233zd(E)) and a bottoms stream comprising the trichlorofluoromethane (R11) and the extractive solvent;
feeding the bottoms stream to a second distillation column; and
separating the trichlorofluoromethane (R11) from the extractive solvent in the second distillation column to form a second overhead stream comprising the trichlorofluoromethane (R11) and a second bottoms stream comprising the extractive solvent.

20. A process according to claim 19, wherein the extractive solvent from the second bottoms stream is recycled to the first distillation column.

* * * * *